US 6,475,772 B1

(12) United States Patent
Kalra et al.

(10) Patent No.: US 6,475,772 B1
(45) Date of Patent: Nov. 5, 2002

(54) STRAIN OF TRICHODERMA HARZIANUM USEFUL AS NEMATODE INHIBITOR, FUNGICIDE AND PLANT GROWTH PROMOTER AND A PROCESS FOR THE ISOLATION THEREOF

(75) Inventors: Alok Kalra, Lucknow (IN); Harikesh Bahadur Singh, Lucknow (IN); Rakesh Pandey, Lucknow (IN); Nirmal Kumar Patra, Lucknow (IN); Neetu Katiyar, Lucknow (IN); Moti Lal Gupta, Lucknow (IN); Om Parkash Dhawan, Lucknow (IN); Sushil Kumar, Lucknow (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 09/755,967

(22) Filed: Jan. 5, 2001

(30) Foreign Application Priority Data

Mar. 31, 2000 (IN) .............................. 368/D/00

(51) Int. Cl.$^7$ .......................... A01N 63/00; C12N 1/00; C12N 1/14; C12N 1/16; C12N 3/00
(52) U.S. Cl. .................... 435/254.6; 435/242; 435/945; 424/93.5; 424/405
(58) Field of Search .............................. 435/242, 254.6, 435/945, 405; 424/405, 93.1, 93.5

(56) References Cited

PUBLICATIONS

Chang et al., "Increased Growth of Plants in the Presence of the Biological Control Agent *Trichoderma harzianum*," *Plant Disease*, pp. 145–147 (Feb. 1986).

Papavizas et al., "Evaluation of New Biotypes of *Trichoderma harzianum* for Tolerance to Benomyl and Enhanced Biocontrol Capabilities," *Phytopathology*, vol. 72, No. 1, pp. 126–131 (1982).

Windham et al., "Effects of *Trichoderma* spp. on Maize Growth and *Meloidogyne arenaria* Reproduction," *Phytopathology*, pp. 493–495 (Jun. 1989).

MacKenzie et al., "Enhanced Root and Shoot Growth of Chrysanthemum Cuttings Propagated with the Fungus *Trichoderma harzianum*," *HortScience*, vol. 30, No. 3, pp. 496–498 (Jun. 1995).

*Primary Examiner*—David M. Naff
*Assistant Examiner*—Deborah Ware
(74) *Attorney, Agent, or Firm*—Merchant & Gould P.C.

(57) ABSTRACT

A strain of *Trichoderma harzianum* is obtained that is useful as a nematode inhibitor, fungicide and plant growth promoter. The strain has ATCC accession number PTA-3701. The strain is isolated by treating *Trichoderma harzianum* isolated from experimental fields of Central Institute of Medicinal and Aromatic Plants (CIMAP) Field Station with a mutagen such as ethyl methyl sulphonate, and isolating a whitish and fast growing strain of *Trichoderma harzianum*.

6 Claims, No Drawings

STRAIN OF TRICHODERMA HARZIANUM USEFUL AS NEMATODE INHIBITOR, FUNGICIDE AND PLANT GROWTH PROMOTER AND A PROCESS FOR THE ISOLATION THEREOF

FIELD OF THE INVENTION

The present invention relates to a novel strain of *Trichoderma harzianum* useful as nematode inhibitor, fungicide and plant growth promoter and a process for the isolation thereof. This novel strain of *Trichoderma harzianum* has been deposited at Central Institute of Medicinal and Aromatic Plants (CIMAP) Type Culture Collection bearing accession No. C-Th-U.

BACKGROUND OF THE INVENTION

From the time seeds/planting propagules are sown/planted in the fields and till their harvesting, plants are exposed to a variety of microorganisms in its environment. These may be beneficial or deleterious to the plants depending on the specific microbe. Plant beneficial microbes preventing the growth or action of plant deleterious microbes are called bio-pesticides and this form of disease prevention is called bio-control. As a subject, bio-control has become more popular during the past few years mainly because of the introduction of more stringent regulations for the use of chemical pesticides. However, it still lacks farmers acceptability; the main reason being that it does not offer any additional benefits over the conventional chemical control. *Trichoderma harzianum* has been used as a bio-control agent to protect the plants against root, seed and foliar diseases.

PRIOR ART RELATING TO THE INVENTION

Some efforts to make this system of plant disease management more attractive have been made and some strains of *Trichoderma harzianum* have been developed/identified providing extra benefits of i) plant growth promotion (Chang et al., 1986, *Plant Disease*, 70,145–148)

ii) resistance to pesticides (Papavizas et al., 1982, *Phytopathology*, 72,126–132) so that the strain can be utilized along with the pesticides in Integrated Pest Management iii) effectiveness against phytonematodes (Windham et. al, 1989, *Phytopathology*, 73, 493–495), iv) induction/enhancement of rooting of stem cuttings in the nursery (Mackenzie et. al, 1995, *HortScience*, 30, 496–498).

Though, the strains produced in these above prior arts possess one of the said advantages, a strain/isolate having more than one property (as mentioned above) would be definitely useful for the farmers/growers. Adopting such system of management of plant diseases as such strain, apart from managing plant pathogenic fungi and phytonematodes, would also contribute to improve plant growth.

Experiments have been carried out and a new strain of *Trichoderma harzianum* has been developed with antagonistic and bio-control potential against soil-borne plant pathogenic fungi and phytonematodes and ability to improve/enhance plant growth.

OBJECTS OF THE INVENTION

The main object of the present invention is to develop a novel strain of *Trichoderma harzianum* which has been deposited at CIMAP Type Culture Collection having accession No. C-TH-U and has been deposited at the American Type Culture Collection (ATCC), Manassas, Va. 20110-2209, USA, on Sep. 11, 2001, having accession No. PTA-3701, with a broader range of antagonistic activities like effectiveness against pathogenic fungi as well as nematodes etc.

Another object of the present invention is to develop novel strain of *Trichoderma harzianum* with additional advantages of plant growth promotion.

Yet another object of the present invention is to isolate a novel strain of *Trichoderma harzianum* from CIMAP field station at Bangalore, India.

SUMMARY OF THE INVENTION

To meet the above objects, the present invention provides a novel strain of *Trichoderma harzianum* and a process for the isolation of the same.

DETAILED DESCRIPTION OF THE INVENTION

Accordingly, the present invention provides a novel strain of *Trichoderma harzianum* useful as nematode inhibitor, fungicide and plant growth promoter which has been deposited at CIMAP Type Culture Collection bearing accession No. C-TH-U and which has been deposited at ATCC bearing accession No. PTA-3701.

The present invention also relates to a process for the isolation of the novel strain of *Trichoderma harzianum* useful as nematode inhibitor, fungicide and plant growth promoter which has been deposited at CIMAP Type Culture Collection bearing accession No. C-Th-U and which has been deposited at ATCC bearing accession No. PTA-3701, said process comprising:

(a) obtaining a spore suspension ranging between $10^3$ to $10^8$/ml. of *Trichoderma harzianum* isolated from experimental fields of CIMAP, Field Station, Bangalore;

(b) treating the conidial suspension with 100–500 ppm concentrations of mutagens such as ethyl methyl sulphonate for 0.5 to 6 hours;

(c) washing the conidia with sterilized distilled water and placing them on Petri plates containing media like potato dextrose agar medium, and selecting an apparently different whitish and fast growing strain out of very few survivals.

In an embodiment of the present invention, the phytopathogenic fungi are selected from the group consisting of *R. solani* and *S. rolfsil.*

In another embodiment of the present invention, the phytonematodes are selected from the group consisting of *M. javanica, Pratylenchus thornei* and *M. incognita.*

In yet another embodiment of the present invention, the host plants are selected from the group consisting of *Rosa damascena, M. arvensis* and *A. pallens.*

The invention is described in detail in the examples given below which are provided to illustrate the invention and therefore should not be considered to limit the scope of present invention.

EXAMPLE-1

Isolation of the Strain

*Trichoderma harzianum* was isolated from the rhizosphere of geranium (*Pelargonium graveolens*) grown at CIMAP Field Station Bangalore, India. The conidial suspension ($10^6$/ml) of *Trichoderma harzianum* was treated with 250 ppm concentration of ethyl methane sulphonate (EMS) in 0.1 M. phosphate buffer (pH 7.0) at 27° C. for 3 hours. Treated spores were washed twice with sterile distilled water and centrifuged at 1000 rpm for 10 minutes to remove EMS and subsequently plated on potato dextrose agar (PDA) medium containing 500 mg $L^{-1}$ Streptomycin sulphate and 150 mg $L^{-1}$ rose bengal. The plates were incubated at 30° C. and the colonies developed (after 5 days) were isolated, purified and subcultured 10 times on PDA to test the stability. A variant (light green colour) was selected. This culture was deposited at Central Institute of Medicinal and Aromatic Plants (CIMAP) Type Culture Collection bearing accession No. C-Th-U and which has been deposited at ATCC bearing accession No. PTA-3701. This strain (designated as CIMAP-C-Th U) was maintained at 30° C. on potato dextrose agar medium and was tested for its fungicidal, nematode inhibitory and growth promoting activities. The characteristics of the new improved *Trichoderma harzianum* strain Th-U is given in Table 1.

TABLE 1

Characteristics of the new improved *Trichoderma harzianum* strain Th U

| | |
|---|---|
| Colour | Light green |
| Growth | Fast growing |
| Antifungal activity | Present |
| Nematicidal activity | Present |
| Plant growth promoting activity | Present |

EXAMPLE-2

As a Biofungicide

The potential to control stem cutting rot (caused by *R. solani*) in geranium (*Pelargonium graveolens*) by the selected strain (Th-U) was investigated in vitro. The earthen pots (9" diameter) were filled with sterilized soil (sandy loam) and inoculated with Th-U and/or *R. solani* (@20 g/kg. soil) grown on sand maize (3:1) medium (SMM). Terminal stem cuttings (6–8") of geranium were planted in these pots after 72 hours of inoculation. Only 9% of cuttings survived in pots inoculated with the pathogenic fungus *R. solani*. Pots receiving *Trichoderma harzianum* in addition to the pathogenic fungus *R. solani* effectively checked the rotting of stem cuttings and the degree of protection provided was at par with fungicide chlorothalonil (found most effective in reducing the cutting rot incidence in our earlier studies: Kalra et al., 1996, *Indian Journal of Mycology* and *Plant Pathology*, 26,125.). More than 70 % of cuttings survived in the pots inoculated with the selected Th-U strain and pathogenic fungus *R. solani* (Table-2).

TABLE 2

Effect of *Trichoderma harzianum* strain Th-U on Rhizoctonia rot of stem cuttings of geranium (cv. Lo.)

| Treatment | Survival of cuttings* (%) |
|---|---|
| Uninfested control | 83 |
| *Rhizoctonia solani* only | 09 |
| Th-U only | 93 |
| *R. solani* + Th-U | 70 |
| *R. solani* + chlorothalonil (0.3% soil drench) | 74 |

*observed after 45 days of planting

EXAMPLE-3

Plant Growth Promotion

The potential of Th-U to enhance the growth and contribute to increased productivity were investigated. Th-U and other isolates of *Trichoderma harzianum* were tested for their growth promoting activities in Japanese mint (*Mentha arvensis*) and the findings were further confirmed on davana (*Artemisia pallens*); the two important essential oil bearing crops.

The earthen pots containing sterilized soil were inoculated with Th-U and other *Trichoderma harzianum* strains/isolates (@20 g/kg soil). Suckers of *M. arvensis* and seedlings of davana (45-days- old) were planted into the inoculated pots after 72 hours of inoculation. Though a few other strains (Th-2 and Th-K) improved the growth and yield of *M. arvensis* marginally, a marked improvement in growth and yield was observed with the strain Th-U (Table 3). Presence of Th-U increased over all weight and essential oil yields of *A. pallens* also (Table 4).

TABLE 3

Evaluation of different isolates of *Trichoderma harzianum* (Th) for increased plant growth and higher yields in Japanese mint (*Mentha arvensis*)

| Th isolates/strain | Plant height (cm) | Total herbage (g) | Oil content (%) | Oil yield (ml) |
|---|---|---|---|---|
| Th-1 | 65 | 122 | 0.50 | 0.60 |
| Th-2 | 70 | 140 | 0.48 | 0.67 |
| Th-K | 70 | 140 | 0.49 | 0.69 |
| Th-B | 66 | 121 | 0.51 | 0.61 |
| Th-U | 78 | 156 | 0.50 | 0.74 |
| Th-3 | 68 | 126 | 0.49 | 0.65 |
| Th-4 | 66 | 120 | 0.50 | 0.60 |
| Check (without Th) | 65 | 127 | 0.48 | 0.62 |

TABLE 4

Effect of *Trichoderma harzianum* on yield and yield components in davana (*Artemisia pallens*) and Japanese mint (*Mentha arvensis*)

| | *Artemisia pallens* | | *Mentha arvensis* | |
|---|---|---|---|---|
| | Untreated | Treated | Untreated | Treated |
| Plant height (cms) | 35.3 | 42.1 | 65 | 78 |
| Total herbage (g/plant) | 25.7 | 32.1 | 127 | 156 |
| Oil content (%) | 0.23 | 0.26 | 0.48 | 0.50 |
| Oil yield (ml/plant) | 0.06 | 0.08 | 0.62 | 0.74 |

EXAMPLE-4

As a Bionematicide

The root knot nematode (*Meloidogyne incognita*) is a major constraint to the successful cultivation of many crops. The efficacy of Th-U and other isolates of *Trichoderma harzianum* in controlling root knot disease in tomato were investigated.

The pots were treated with *Trichoderma harzianum* strains 1, 2, 3, 4 and Th-U (@20 g/kg soil) and 30 days old tomato seedlings were planted 72 hours after inoculation of *Trichoderma harzianum*. Seven days after planting seedlings were inoculated with *M. incognita* (@ 1000 larvae/kg soil). It is clear from the results presented in Table 5 that Th-U is relatively more effective in reducing root knot severity compared to other strains.

In another experiment, the potential of Th-U on *Matricaria chamomilla* and *Ocimum basilicum* grown with and without *M. incognita* were investigated in earthen pots. The pots were treated with Th-U (@20 g/kg soil) grown on SMM and seedlings of said plants were planted 72 hours after inoculation. Seedlings were inoculated with *M. incognita* (@ 1000 larvae/kg soil), one week after transplanting. Th-U treated pots produced more herbage, which in turn yielded more essential oil. Soil infestation with Th-U resulted in lower root knot index values and reduction in the population of *M. incognita* in roots and rhizosphere (Table-6).

TABLE 5

Evaluation of different *Trichoderma harzianum* (Th) strains for nematode inhibitory properties in tomato.

| Th strains | Root knot index value* | Total nematode population |
|---|---|---|
| Th 1 | 2.66 | 3430 |
| Th 2 | 2.00 | 3100 |
| Th 3 | 2.33 | 3200 |
| Th 4 | 2.00 | 2910 |
| Th U | 1.66 | 2412 |
| Check (no Trichoderma) | 3.00 | 4100 |

TABLE 6

Effect of *Trichoderma harzianum* strain Th-U on root knot disease caused by *Meloidogyne incognita* of *Matricaria chamomilla* (Mc) and *Ocimum basilicum* (Ob).

| Host | Treatment | Total nematode population | Root Knot index | Root Weight (g) | Total Herbage (g) | Oil content (%) | Oil yield (ml) |
|---|---|---|---|---|---|---|---|
| Ob | Untreated | — | — | 5 | 42 | 0.54 | 0.23 |
|  | Mi only | 3696 | 4.0 | 3 | 17 | 0.40 | 0.07 |
|  | Th-U Only | — | — | 7 | 49 | 0.60 | 0.30 |
|  | Th + Mi | 2337 | 2.7 | 5 | 46 | 0.60 | 0.27 |
| Mc | Untreated | — | — | 2 | 14 | Nd | Nd |
|  | Mi only | 3268 | 4.0 | 1 | 8 | Nd | Nd |
|  | Th-U only | — | — | 3 | 24 | Nd | Nd |
|  | Th + Mi | 1741 | 2.6 | 2 | 22 | Nd | Nd |

Nd = Not determined

Advantages

The above mentioned experiments clearly indicate that the developed strain of *Trichoderma harzianum* can be successfully used for the control of soil borne pathogenic fungi and has several advantages over other isolates like (a) ability to improve plant growth (b) potential to suppress plant root knot nematodes. These advantages are tabulated in Table 7.

TABLE 7

Characteristics of different strains of *Trichoderma harzianum* in comparison to strain Th U developed by CIMPA

| Property | Th-1 | Th-2 | Th-3 | Th-4 |
|---|---|---|---|---|
| Color (after sporulation) | Dark green | Green | Green | Light green |
| *Growth (mm) | 81 | 92 | 91 | 90 |
| Antifungal activity | + | + | + | + |
| Nematicidal activity | − | − | + | ++ |
| Plant growth promotion | − | + | − | ++ |

TABLE 7-continued

Characteristics of different strains of *Trichoderma harzianum* in comparison to strain Th U developed by CIMPA

| Property | Th-1 | Th-2 | Th-3 | Th-4 |
|---|---|---|---|---| as observed on Potato dextrose agar plates after 72 hoursours

The application of this strain (Th-U) as a bio-control agent of soil-borne fungal pathogens would have additional advantages of:

1) improvement of plant growth and economic yield of crop plants.
2) its contribution to the reduction of deleterious nematode population in the host tissue and rhizosphere and thereby reducing the severity of root knot disease.
3) its use as soil amendment in reducing the application of hazardous chemical fungicides and nematicides which disturb the natural beneficial soil microflora and pollute the soil and soil water.
4) application of this strain in nursery in reducing the input of chemical fungicides (to protect the cuttings from rooting and various other diseases) which sometime inhibit the rooting of cuttings.
5) its use as organic/biofertiliser in substituting the chemical fertilizers and there by reducing the fertilizer.
6) its three pronged function as a biofungicides, bionemeticides and biofertiliser.

What is claimed is:

1. A biologically pure strain of *Trichoderma harzianum* having neraode inhibitor activity, fungicidal activity and plant growth promoter activity which has been deposited at ATCC as accession No. PTA-3701.

2. A process for the isolation of a biologically pure stain of *Trichoderma harzianuzn* having fungicidal activity against phytopathogenic fungus, having inhibitor activity against phytonematode, and having plant growth promoter activity, and which has ATCC accession No. PTA-3701, said process comprising: (a) obtaining a spore suspension having $10^3$ to $10^8$ cells/ml. of *Trichoderma harzianrum* isolated from experimental fields of Central Institute of Medicinal and Aromai Plants (CIMAP) Field Station, Bangalore, India; (b) treating the spore suspension with 100–500 ppm of ethyl methyl sulphonate rnutagen for 0.5 to 6 hours; (c) washing the treated spores with sterilized distilled water and placing the spores in Petri plates containing a growth medium for the spores; and (d) selecting and isolating a whitish and fast growing strain of *Trichoderma harzianum* as said biologically pure strain of *Trichoderma harzianum*.

3. A process as claimed in claim 2, wherein the phytopathogenic fungus is selected from the group consisting of *R. solani* and *S. rolfsii*.

4. A process as claimed in claims 2, wherein the phytonematode is selected from the group consisting of *M. incognita, M. javanica* and *P. thornei*.

5. A process as claimed in claim 2, wherein the plant is selected from the group consisting of *M. arvensis, A. pallens* and *R. damascena*.

6. A process as claimed in claim 2, wherein the growth medium is potato dextrose agar.

* * * * *